(12) United States Patent
Rade et al.

(10) Patent No.: US 11,426,588 B2
(45) Date of Patent: Aug. 30, 2022

(54) SYSTEMS AND METHODS FOR ARBITRARY CURRENT WAVEFORM GENERATION

(71) Applicant: Advanced Neuromodulation Systems, Inc., Plano, TX (US)

(72) Inventors: Gavin Rade, Dallas, TX (US); Daran DeShazo, Lewisville, TX (US)

(73) Assignee: ADVANCED NEUROMODULATION SYSTEMS, INC., Plano, TX (US)

( * ) Notice: Subject to any disclaimer, the term of this patent is extended or adjusted under 35 U.S.C. 154(b) by 167 days.

(21) Appl. No.: 16/855,211

(22) Filed: Apr. 22, 2020

(65) Prior Publication Data

US 2021/0330982 A1 Oct. 28, 2021

(51) Int. Cl.
*A61N 1/36* (2006.01)
*A61N 1/02* (2006.01)

(52) U.S. Cl.
CPC ......... *A61N 1/36157* (2013.01); *A61N 1/025* (2013.01); *A61N 1/36125* (2013.01)

(58) Field of Classification Search
CPC . A61N 1/36157; A61N 1/025; A61N 1/36125
See application file for complete search history.

(56) References Cited

U.S. PATENT DOCUMENTS

| | | | |
|---|---|---|---|
| 8,615,306 B2 | 12/2013 | Griffith | |
| 8,706,212 B2 | 4/2014 | Ternes et al. | |
| 9,008,790 B2 | 4/2015 | Griffith et al. | |
| 9,138,582 B2 | 9/2015 | Doan et al. | |
| 9,155,892 B2 | 10/2015 | Parker et al. | |
| 9,248,292 B2 | 2/2016 | Trier et al. | |
| 9,446,231 B2 | 9/2016 | Carbunaru et al. | |
| 9,566,449 B2 | 2/2017 | Perryman et al. | |
| 9,649,492 B2 | 5/2017 | Li et al. | |
| 9,895,542 B2 | 2/2018 | Baru et al. | |

(Continued)

FOREIGN PATENT DOCUMENTS

EP 2508224 A1 10/2012

OTHER PUBLICATIONS

International Search Report and Written Opinion for International Patent Application No. PCT/US2021/028359, dated Jul. 2, 2021, 12 pages.

*Primary Examiner* — Paula J Stice
(74) *Attorney, Agent, or Firm* — Armstrong Teasdale LLP

(57) ABSTRACT

The present disclosure provides systems and methods for generating waveforms for an implantable pulse generator of a neurostimulation system. A waveform generation system includes a computing device, at least one buffer memory, and at least one programmable current regulator. The at least one buffer memory is coupled between the computing device and the at least one programmable current regulator. The computing device is configured to load a string of output current values into the at least one buffer memory, and the at least one buffer memory is configured to sequentially feed each output current value to the at least one programmable current regulator. Further, the at least one programmable current regulator is configured to control current supplied to a plurality of electrodes based on the received output current values.

14 Claims, 4 Drawing Sheets

(56) References Cited

U.S. PATENT DOCUMENTS

| | | |
|---|---|---|
| 10,213,603 B2 | 2/2019 | Trier et al. |
| 2005/0010625 A1 | 1/2005 | Andrews |
| 2007/0078498 A1 | 4/2007 | Rezai et al. |
| 2012/0259383 A1* | 10/2012 | Trier .................... G06F 1/0328 607/46 |
| 2018/0071513 A1* | 3/2018 | Weiss ....................... A61N 1/36 |

* cited by examiner

SYSTEMS AND METHODS FOR ARBITRARY CURRENT WAVEFORM GENERATION

A. FIELD OF THE DISCLOSURE

The present disclosure relates generally to neurostimulation systems, and more particularly to generating high-resolution arbitrary neuromodulation waveforms.

B. BACKGROUND ART

Neurostimulation is an established neuromodulation therapy for the treatment of chronic pain and movement disorders. For example, neurostimulation has been shown to improve cardinal motor symptoms of Parkinson's Disease (PD), such as bradykinesia, rigidity, and tremors in addition to relieving symptoms of failed back surgery syndrome (FBSS) and complex regional pain syndrome (CRPS). Types of neurostimulation include deep brain stimulation (DBS), spinal cord stimulation (SCS), and Dorsal Root Ganglion (DRG) stimulation.

Recently, novel waveform therapy for neuromodulation has become a topic of interest, and there is a desire to create arbitrary waveforms. However, at least some known systems are only capable of producing a waveform as a series of square pulses at a repeating frequency and pulse width. The frequency may be limited to, for example, a maximum of 10 kilohertz (kHz). Further, the pulse width may be limited to, for example, a minimum of 10 microseconds (μs). In addition, each pulse generally has a fixed amplitude, and the amplitude does not vary within the pulse. Thus, within these constraints of at least some known systems, it may be difficult or impossible to generate more complicated waveforms.

Accordingly, it would be desirable to provide a system that facilitates generating a plurality of different types of waveforms, including waveforms with relatively complicated characteristics.

BRIEF SUMMARY OF THE DISCLOSURE

In one embodiment, the present disclosure is directed to a waveform generation system for an implantable pulse generator of a neurostimulation system. The waveform generation system includes a computing device, at least one buffer memory, and at least one programmable current regulator, wherein the at least one buffer memory is coupled between the computing device and the at least one programmable current regulator, wherein the computing device is configured to load a string of output current values into the at least one buffer memory, wherein the at least one buffer memory is configured to sequentially feed each output current value to the at least one programmable current regulator, and wherein the at least one programmable current regulator is configured to control current supplied to a plurality of electrodes based on the received output current values.

In another embodiment, the present disclosure is directed to a neurostimulation system. The neurostimulation system includes a plurality of electrodes and a waveform generation system coupled to the plurality of electrodes. The waveform generation system includes a computing device, at least one buffer memory, and at least one programmable current regulator, wherein the at least one buffer memory is coupled between the computing device and the at least one programmable current regulator, wherein the computing device is configured to load a string of output current values into the at least one buffer memory, wherein the at least one buffer memory is configured to sequentially feed each output current value to the at least one programmable current regulator, and wherein the at least one programmable current regulator is configured to control current supplied to the plurality of electrodes based on the received output current values.

In another embodiment, the present disclosure is directed to a method of assembling a waveform generation system for use in an implantable pulse generator of a neurostimulation system. The method includes coupling at least one buffer memory to computing device, and coupling at least one programmable current regulator to the at least one buffer memory, wherein the computing device is configured to load a string of output current values into the at least one buffer memory, wherein the at least one buffer memory is configured to sequentially feed each output current value to the at least one programmable current regulator, and wherein the at least one programmable current regulator is configured to control current supplied to a plurality of electrodes based on the received output current values.

The foregoing and other aspects, features, details, utilities and advantages of the present disclosure will be apparent from reading the following description and claims, and from reviewing the accompanying drawings.

BRIEF DESCRIPTION OF THE DRAWINGS

Corresponding reference characters indicate corresponding parts throughout the several views of the drawings.

DETAILED DESCRIPTION OF THE DISCLOSURE

Figure 1:
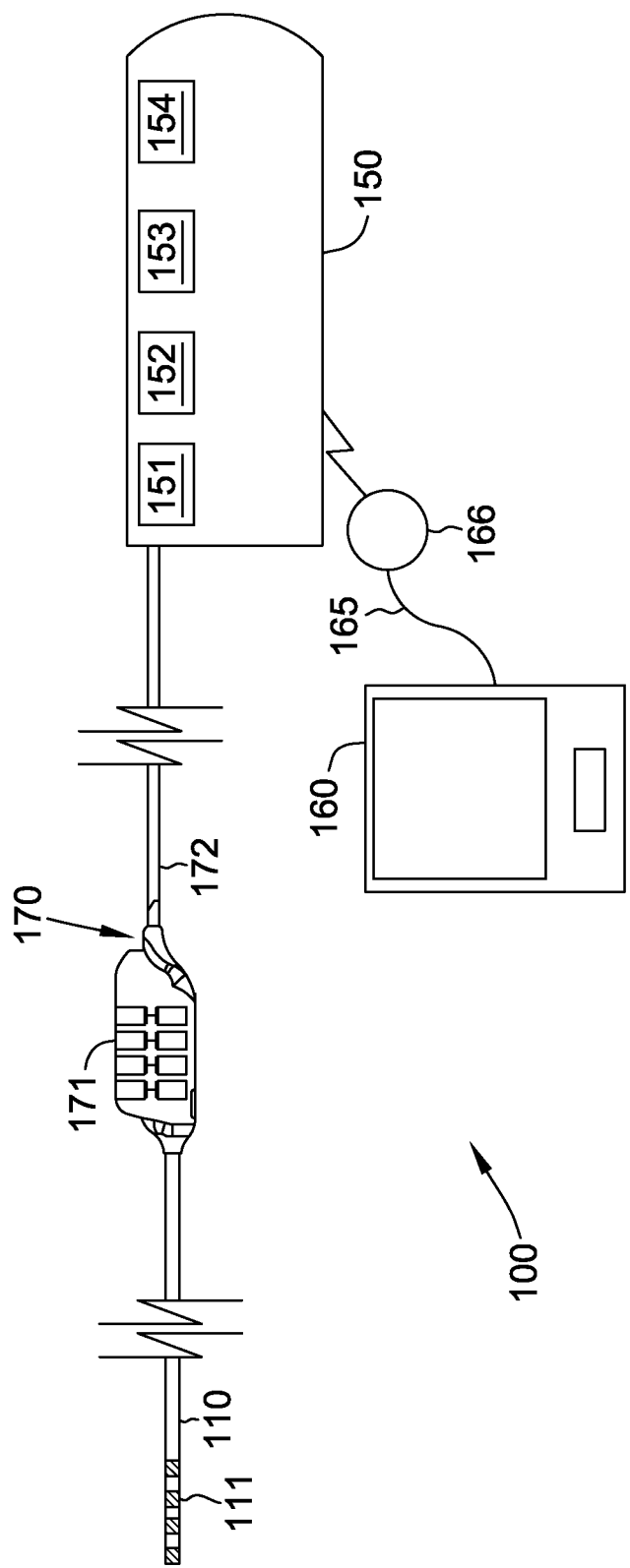
FIG. 1 is a schematic view of one embodiment of a stimulation system.

The present disclosure provides systems and methods for generating waveforms for an implantable pulse generator of a neurostimulation system. A waveform generation system includes a computing device, at least one buffer memory, and at least one programmable current regulator. The at least one buffer memory is coupled between the computing device and the at least one programmable current regulator. The computing device is configured to load a string of output current values into the at least one buffer memory, and the at least one buffer memory is configured to sequentially feed each output current value to the at least one programmable current regulator. Further, the at least one programmable current regulator is configured to control current supplied to a plurality of electrodes based on the received output current values.

As compared to at least some known systems, the systems and methods described herein allow for using higher frequencies, shorter pulse widths, and varying amplitudes, when generating stimulation waveforms. This enables generating more complicated waveforms that may not be producible using at least some known systems.

More specifically, the embodiments described herein facilitate changing an output current of a current regulator or current mirror rapidly (e.g., as fast as every microsecond), enabling creation of waveforms that closely approximate continuous signals. For example, waveforms may be generated from abutting square wave pulses with varying amplitudes, as described herein. Waveforms generated using the systems and methods described herein may approximate, for example, sine waves, triangle waves, noise spectrums, etc.

As described herein, the systems and methods herein may be implemented using a microcontroller unit (MCU) or memory device with direct memory access (DMA), an amplitude buffer memory, and an architecture for programmatically generating current.

Neurostimulation systems are devices that generate electrical pulses and deliver the pulses to nervous tissue of a patient to treat a variety of disorders. One category of neurostimulation systems is deep brain stimulation (DBS). In DBS, pulses of electrical current are delivered to target regions of a subject's brain, for example, for the treatment of movement and effective disorders such as PD and essential tremor. Another category of neurostimulation systems is spinal cord stimulation (SCS) for the treatment of chronic pain and similar disorders.

Neurostimulation systems generally include a pulse generator and one or more leads. A stimulation lead includes a lead body of insulative material that encloses wire conductors. The distal end of the stimulation lead includes multiple electrodes, or contacts, that intimately impinge upon patient tissue and are electrically coupled to the wire conductors. The proximal end of the lead body includes multiple terminals (also electrically coupled to the wire conductors) that are adapted to receive electrical pulses. In DBS systems, the distal end of the stimulation lead is implanted within the brain tissue to deliver the electrical pulses. The stimulation leads are then tunneled to another location within the patient's body to be electrically connected with a pulse generator or, alternatively, to an "extension." The pulse generator is typically implanted in the patient within a subcutaneous pocket created during the implantation procedure.

The pulse generator is typically implemented using a metallic housing (or can) that encloses circuitry for generating the electrical stimulation pulses, control circuitry, communication circuitry, a rechargeable battery, etc. The pulse generating circuitry is coupled to one or more stimulation leads through electrical connections provided in a "header" of the pulse generator. Specifically, feedthrough wires typically exit the metallic housing and enter into a header structure of a moldable material. Within the header structure, the feedthrough wires are electrically coupled to annular electrical connectors. The header structure holds the annular connectors in a fixed arrangement that corresponds to the arrangement of terminals on the proximal end of a stimulation lead.

Referring now to the drawings, and in particular to FIG. 1, a stimulation system is indicated generally at 100. Stimulation system 100 generates electrical pulses for application to tissue of a patient, or subject, according to one embodiment. System 100 includes an implantable pulse generator (IPG) 150 that is adapted to generate electrical pulses for application to tissue of a patient. Alternatively, system 100 may include an external pulse generator (EPG) positioned outside the patient's body. IPG 150 typically includes a metallic housing (or can) that encloses a controller 151, pulse generating circuitry 152, a battery 153, far-field and/or near field communication circuitry 154, and other appropriate circuitry and components of the device. Controller 151 typically includes a microcontroller or other suitable processor for controlling the various other components of the device. Software code is typically stored in memory of IPG 150 for execution by the microcontroller or processor to control the various components of the device.

IPG 150 may comprise one or more attached extension components 170 or be connected to one or more separate extension components 170. Alternatively, one or more stimulation leads 110 may be connected directly to IPG 150. Within IPG 150, electrical pulses are generated by pulse generating circuitry 152 and are provided to switching circuitry. The switching circuit connects to output wires, traces, lines, or the like (not shown) which are, in turn, electrically coupled to internal conductive wires (not shown) of a lead body 172 of extension component 170. The conductive wires, in turn, are electrically coupled to electrical connectors (e.g., "Bal-Seal" connectors) within connector portion 171 of extension component 170. The terminals of one or more stimulation leads 110 are inserted within connector portion 171 for electrical connection with respective connectors. Thereby, the pulses originating from IPG 150 and conducted through the conductors of lead body 172 are provided to stimulation lead 110. The pulses are then conducted through the conductors of lead 110 and applied to tissue of a patient via electrodes 111. Any suitable known or later developed design may be employed for connector portion 171.

For implementation of the components within IPG 150, a processor and associated charge control circuitry for an implantable pulse generator is described in U.S. Pat. No. 7,571,007, entitled "SYSTEMS AND METHODS FOR USE IN PULSE GENERATION," which is incorporated herein by reference. Circuitry for recharging a rechargeable battery of an implantable pulse generator using inductive coupling and external charging circuits are described in U.S. Pat. No. 7,212,110, entitled "IMPLANTABLE DEVICE AND SYSTEM FOR WIRELESS COMMUNICATION," which is incorporated herein by reference.

An example and discussion of "constant current" pulse generating circuitry is provided in U.S. Patent Publication No. 2006/0170486 entitled "PULSE GENERATOR HAVING AN EFFICIENT FRACTIONAL VOLTAGE CONVERTER AND METHOD OF USE," which is incorporated herein by reference. One or multiple sets of such circuitry may be provided within IPG 150. Different pulses on different electrodes may be generated using a single set of pulse generating circuitry using consecutively generated pulses according to a "multi-stimset program" as is known in the art. Alternatively, multiple sets of such circuitry may be employed to provide pulse patterns that include simultaneously generated and delivered stimulation pulses through various electrodes of one or more stimulation leads as is also known in the art. Various sets of parameters may define the pulse characteristics and pulse timing for the pulses applied to various electrodes as is known in the art. Although constant current pulse generating circuitry is contemplated for some embodiments, any other suitable type of pulse generating circuitry may be employed such as constant voltage pulse generating circuitry.

Stimulation lead(s) 110 may include a lead body of insulative material about a plurality of conductors within the material that extend from a proximal end of lead 110 to its distal end. The conductors electrically couple a plurality of electrodes 111 to a plurality of terminals (not shown) of lead 110. The terminals are adapted to receive electrical pulses and the electrodes 111 are adapted to apply stimulation pulses to tissue of the patient. Also, sensing of physiological signals may occur through electrodes 111, the conductors, and the terminals. Additionally or alternatively, various sensors (not shown) may be located near the distal end of stimulation lead 110 and electrically coupled to terminals through conductors within the lead body 172. Stimulation lead 110 may include any suitable number and type of electrodes 111, terminals, and internal conductors.

Controller device 160 may be implemented to recharge battery 153 of IPG 150 (although a separate recharging device could alternatively be employed). A "wand" 165 may be electrically connected to controller device through suitable electrical connectors (not shown). The electrical connectors are electrically connected to coil 166 (the "primary" coil) at the distal end of wand 165 through respective wires (not shown). Typically, coil 166 is connected to the wires through capacitors (not shown). Also, in some embodiments, wand 165 may comprise one or more temperature sensors for use during charging operations.

The patient then places the primary coil 166 against the patient's body immediately above the secondary coil (not shown), i.e., the coil of the implantable medical device. Preferably, the primary coil 166 and the secondary coil are aligned in a coaxial manner by the patient for efficiency of the coupling between the primary and secondary coils. Controller device 160 generates an AC-signal to drive current through coil 166 of wand 165. Assuming that primary coil 166 and secondary coil are suitably positioned relative to each other, the secondary coil is disposed within the magnetic field generated by the current driven through primary coil 166. Current is then induced by a magnetic field in the secondary coil. The current induced in the coil of the implantable pulse generator is rectified and regulated to recharge the battery of IPG 150. The charging circuitry may also communicate status messages to controller device 160 during charging operations using pulse-loading or any other suitable technique. For example, controller device 160 may communicate the coupling status, charging status, charge completion status, etc.

External controller device 160 is also a device that permits the operations of IPG 150 to be controlled by a user after IPG 150 is implanted within a patient, although in alternative embodiments separate devices are employed for charging and programming. Also, multiple controller devices may be provided for different types of users (e.g., the patient or a clinician). Controller device 160 can be implemented by utilizing a suitable handheld processor-based system that possesses wireless communication capabilities. Software is typically stored in memory of controller device 160 to control the various operations of controller device 160. Also, the wireless communication functionality of controller device 160 can be integrated within the handheld device package or provided as a separate attachable device. The interface functionality of controller device 160 is implemented using suitable software code for interacting with the user and using the wireless communication capabilities to conduct communications with IPG 150.

Controller device 160 preferably provides one or more user interfaces to allow the user to operate IPG 150 according to one or more stimulation programs to treat the patient's disorder(s). Each stimulation program may include one or more sets of stimulation parameters including pulse amplitude, pulse width, pulse frequency or inter-pulse period, pulse repetition parameter (e.g., number of times for a given pulse to be repeated for respective stimset during execution of program), etc. In the methods and systems described herein, stimulation parameters may include, for example, a number of pulses in a burst (e.g., 3, 4, or 5 pulses per burst), an intra-burst frequency (e.g., 500 Hz), an inter-burst frequency (e.g., 40 Hz), and a delay between the pulses in a burst (e.g., less than 1 millisecond (ms)).

IPG 150 modifies its internal parameters in response to the control signals from controller device 160 to vary the stimulation characteristics of stimulation pulses transmitted through stimulation lead 110 to the tissue of the patient. Neurostimulation systems, stimsets, and multi-stimset programs are discussed in PCT Publication No. WO 2001/093953, entitled "NEUROMODULATION THERAPY SYSTEM," and U.S. Pat. No. 7,228,179, entitled "METHOD AND APPARATUS FOR PROVIDING COMPLEX TISSUE STIMULATION PATTERNS," which are incorporated herein by reference. Example commercially available neurostimulation systems include the EON MINI™ pulse generator and RAPID PROGRAMMER™ device from Abbott Laboratories.

As noted above, the embodiments described herein facilitate changing an output current of a current regulator or current mirror rapidly to create waveforms that may, for example, closely approximate continuous signals. For example, waveforms generated using the systems and methods described herein may approximate sine waves, triangle waves, noise spectrums, etc. The embodiments described herein may be implemented within both SCS and DBS stimulation systems.

Figure 2:
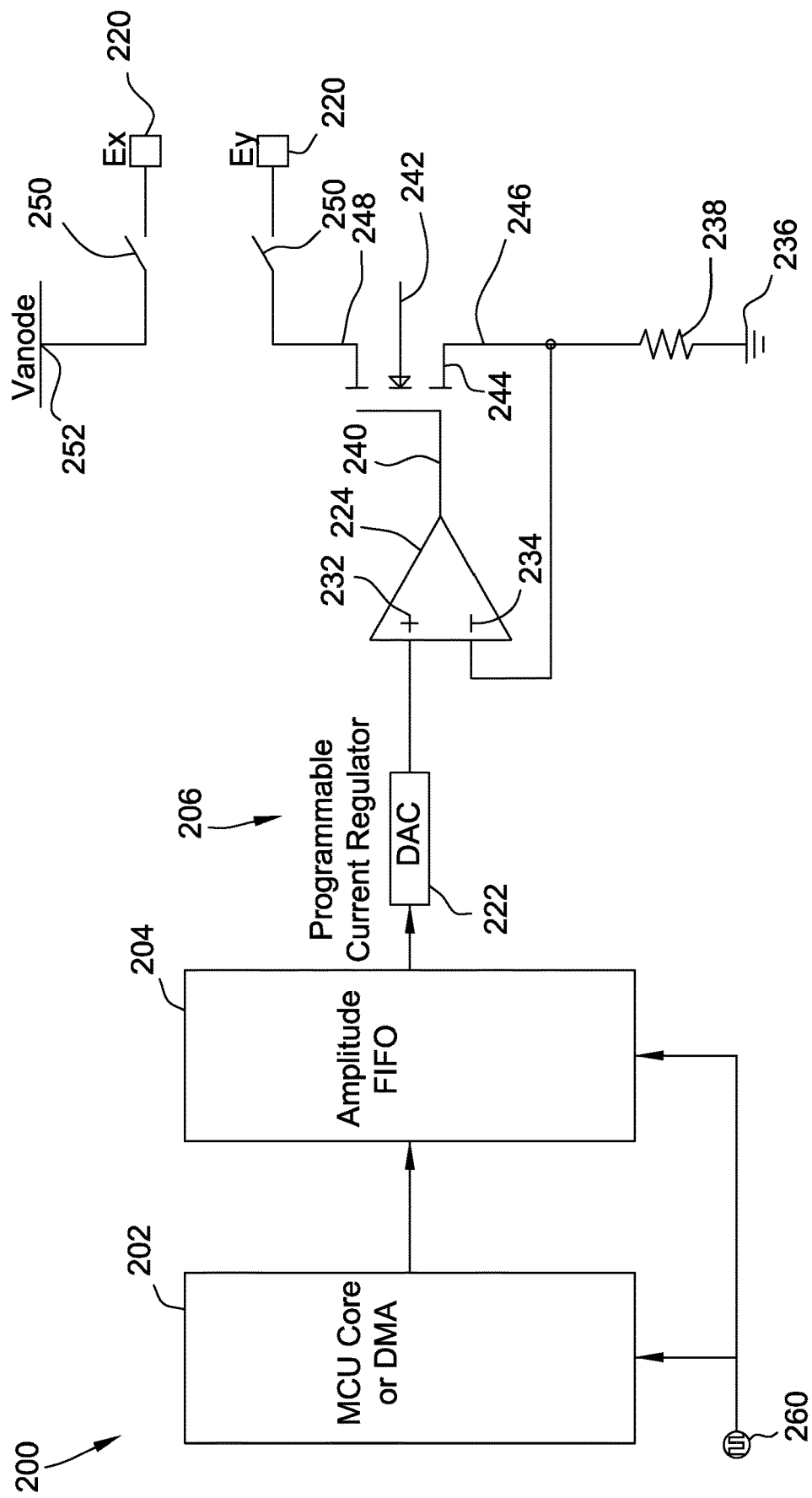
FIG. 2 is a schematic diagram of one embodiment of a waveform generation system.

FIG. 2 is a schematic diagram of one embodiment of a waveform generation system 200. Waveform generation system 200 includes a computing device 202, a buffer memory 204, and a programmable current regulator 206. Waveform generation system 200 may be implemented, for example, within stimulation system 100 (shown in FIG. 1).

In this embodiment, computing device 202 is communicatively coupled to buffer memory 204, and loads buffer memory 204 with a desired current output sequence. Computing device 202 may be, for example, a microcontroller unit (MCU) or a memory device with direct memory access (DMA). Alternatively, computing device 202 may be any computing device capable of performing the functions described herein.

Buffer memory 204 is communicatively coupled between computing device 202 and programmable current regulator 206. In this embodiment, buffer memory 204 is a first in first out (FIFO) buffer memory. Accordingly, buffer memory 204 receives a string of output current values from computing device 202, and outputs those output current values to programmable current regulator 206 in the same order that the output current values were received.

Programmable current regulator 206 controls the current output to a plurality of electrodes 220 based on the output current values received from buffer memory 204. In this embodiment, programmable current regulator 206 includes a digital to analog converter (DAC) 222 that controls a current regulator amplifier 224.

Specifically, as shown in FIG. 2, DAC 222 is coupled to a non-inverting input 232 of current regulator amplifier 224, and an inverting input 234 of current regulator amplifier 224 is coupled to ground 236 through a programmable resistance 238. Further, an output 240 of current regulator amplifier 224 controls the current through a field effect transistor (FET) 242.

In this embodiment, FET 242 is an N-channel MOSFET having a gate 244 coupled to output 240, a source 246 coupled to inverting input 234, and a drain 248 selectively coupleable to electrodes 220 through switches 250. Electrodes 220 are also selectively couplable to an anode voltage 252 through switches 250. Those of skill in the art will appreciate that other architectures may be used without departing from the spirit and scope of the disclosure.

As shown in FIG. 2, in this embodiment, computing device 202 and buffer memory 204 share a same clock signal 260. This may be implemented by using a shared clock for computing device 202 and buffer memory 204, or using independent clocks that are synchronized with one another for computing device 202 and buffer memory 204.

As will appreciated by those of skill in the art, clock signal 260 includes a plurality of edges occurring at regular intervals (e.g., every 500 nanoseconds (ns)). In this embodiment, computing device 202 loads output current values into buffer memory 204, and at each edge, buffer memory 204 feeds one of the output current values into programmable current regulator 206, to cause programmable current regulator 206 to supply current at the output current value to electrodes 220.

Waveform generation system 200 is capable of reversing the direction of current flow by inverting the connections between FET 242 and anode voltage 252. This scheme allows active discharge of the electrodes without any signal excursions below ground 236.

Figure 3:
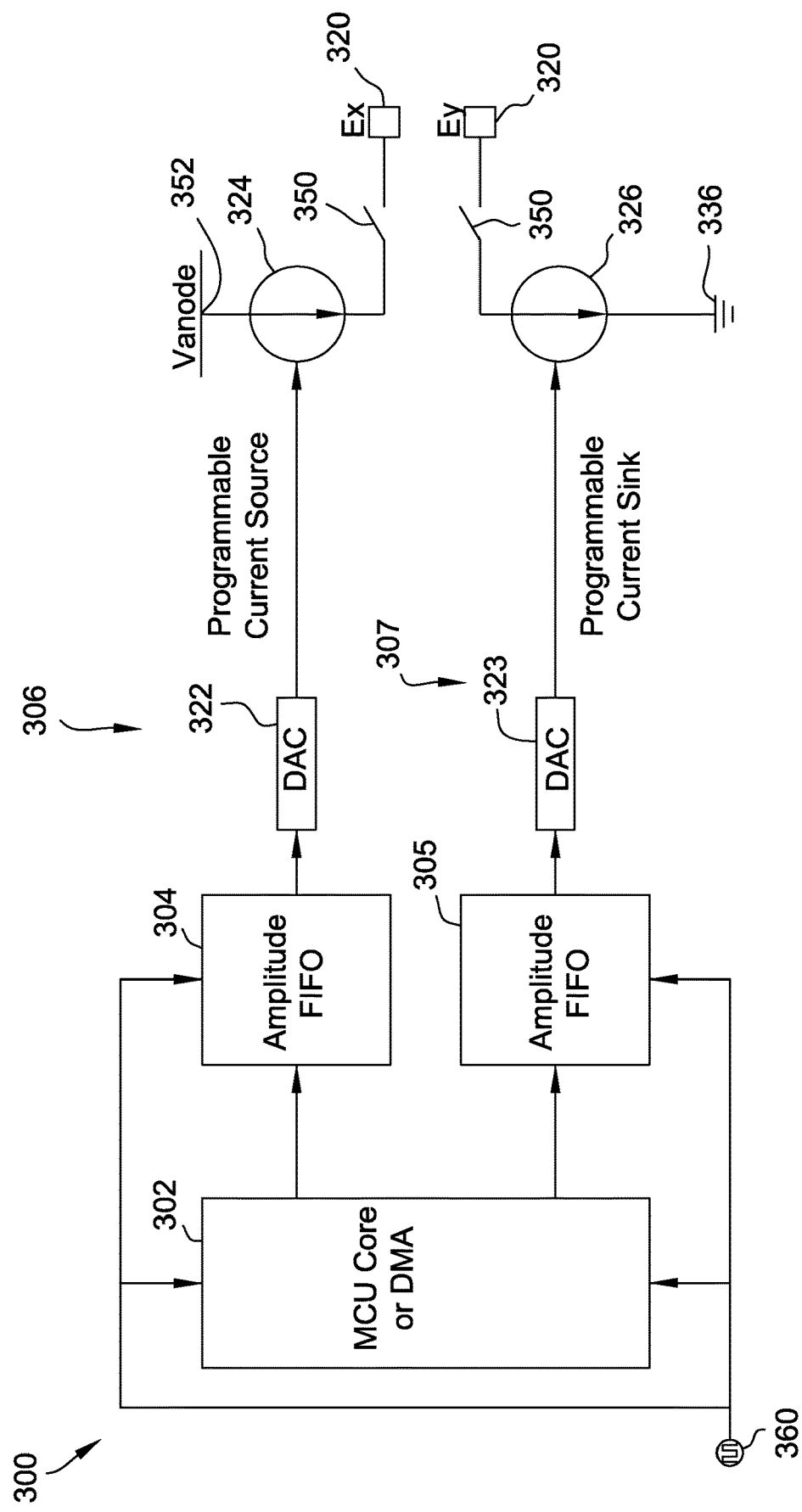
FIG. 3 is a schematic diagram of another embodiment of a waveform generation system.

FIG. 3 is a schematic diagram of an alternative embodiment of a waveform generation system 300. Unless otherwise indicated, waveform generation system 300 functions substantially similar to waveform generation system 200 (shown in FIG. 2). Similar to waveform generation system 200, waveform generation system 300 includes a computing device 302. However, waveform generation system 300 includes a first buffer memory 304, a second buffer memory 305, a first programmable current regulator 306, and a second programmable current regulator 307. In some embodiments, first and second buffer memories 304 and 305 may be consolidated in a single buffer memory.

First buffer memory 304 is coupled between computing device 302 and first programmable current regulator 306, and second buffer memory 305 is coupled between computing device 302 and second programmable current regulator 307. Waveform generation system 300 may be implemented, for example, within stimulation system 100 (shown in FIG. 1).

In this embodiment, computing device 302 loads each of first and second buffer memories 304 and 305 with a respective desired current output sequence. Computing device 302 may be, for example, a MCU or a memory device with DMA. Alternatively, computing device 302 may be any computing device capable of performing the functions described herein.

In this embodiment, first and second buffer memories 304 and 305 are each a first in first out (FIFO) buffer memory. Accordingly, first and second buffer memories 304 and 305 receive a string of output current values from computing device 302, and outputs those output current values to first and second programmable current regulators 306 and 307 in the same order that the output current values were received.

First and second programmable current regulators 306 and 307 control the current output to a plurality of electrodes 320 based on the output current values received from first and second buffer memories 304 and 305, respectively. In this embodiment, first and second programmable current regulators 306 and 307 each include a digital to analog converter (DAC) 322 and 323 that controls one of a programmable current source 324 and a programmable current sink 326. In some embodiments, DACs 322 and 323 may be consolidated in a single buffer memory.

As shown in FIG. 3, programmable current source 324 is coupled to an anode voltage 352, and programmable current sink 326 is coupled to ground 336. Further, electrodes 320 are selectively couplable to programmable current source 324 and programmable current sink 326 through switches 350. Those of skill in the art will appreciate that other architectures may be used without departing from the spirit and scope of the disclosure.

In this embodiment, computing device 302 and first and second buffer memories 304 and 305 share a same clock signal 360. This may be implemented by using a shared clock or using independent clocks that are synchronized with one another for at least some of the components.

As will appreciated by those of skill in the art, clock signal 360 includes a plurality of edges occurring at regular intervals (e.g., every 500 nanoseconds (ns)). In this embodiment, computing device 302 loads output current values into first and second buffer memories 304 and 305, and at each edge, first and second buffer memories 304 and 305 feeds one of the output current values into first and second programmable current regulators 306 and 307, respectively, to cause first and second programmable current regulators 306 and 307 to supply the output current values to electrodes 320.

Because current can be pushed and pulled in either direction using programmable current source 324 and programmable current sink 326, electrodes 320 need not be inverted to apply active discharge waveforms.

Using the embodiments described herein, waveforms that may not be producible using at least some known systems may be generated. Specifically, using a buffer memory, at least one DAC, and at least one programmable current source, as described herein, facilitates rapidly changing output current applied to electrodes, enabling creation of waveforms that closely approximate continuous signals.

Figure 4:
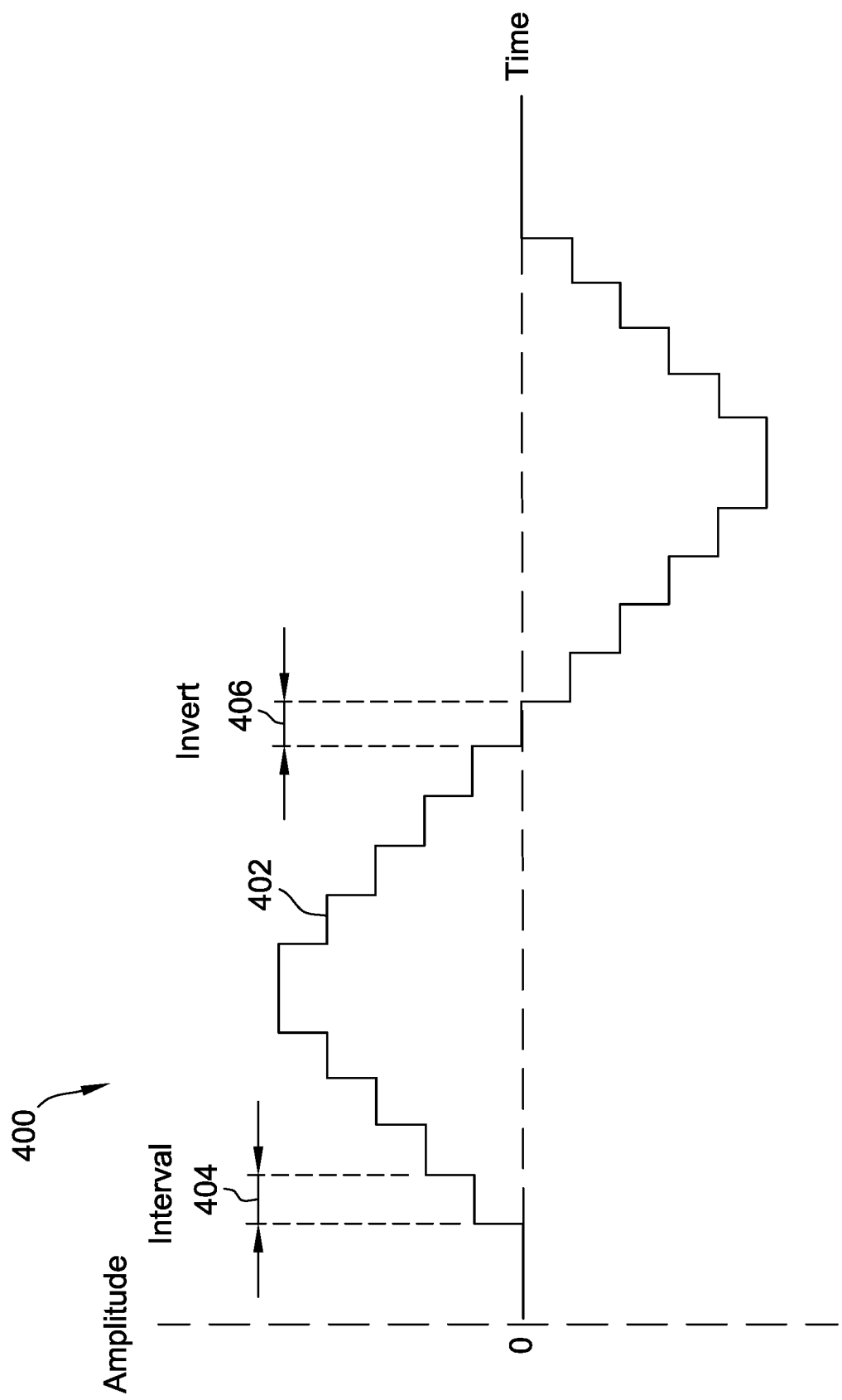
FIG. 4 is an example waveform that may be generated using the systems and methods described herein.

For example, using the systems and methods described herein, waveforms may be generated from abutting square wave pulses with varying amplitudes. FIG. 4 is an example of a waveform 400 that may be generated using the systems and methods described herein. For example, waveform 400 may be generated using waveform generation system 200 or waveform generation system 300.

As shown in FIG. 4, waveform 400 approximates a sinusoidal waveform, and is built from a plurality of abutting square wave pulses 402. That is, at each interval 404, a square wave pulse 402 having a predetermined amplitude is generated. By changing the amplitude between adjacent square wave pulses 402, waveform 400 is generated. The length of interval 404 may be, for example, 500 ns, resulting in an overall pulse sequence of 12 µs.

Those of skill in the art will appreciate that waveform 400 is only an example, and that many different types of waveforms may be generated using the systems and methods described herein.

In some embodiments, it may be desirable to intermittently discharge any charge built up on the electrodes. For example, accumulated charge may be discharged during an inversion period 406 (i.e., a period that marks the transition between positive and negative pulses).

The embodiments described herein provide systems and methods for generating waveforms for an implantable pulse generator of a neurostimulation system. A waveform generation system includes a computing device, at least one buffer memory, and at least one programmable current regulator, The at least one buffer memory is coupled between the computing device and the at least one programmable current regulator. The computing device is configured to load a string of output current values into the at least one buffer memory, and the at least one buffer memory is configured to sequentially feed each output current value to the at least one programmable current regulator. Further, the at least one programmable current regulator is configured to control current supplied to a plurality of electrodes based on the received output current values.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. A waveform generation system for an implantable pulse generator of a neurostimulation system, the waveform generation system comprising:
   a computing device;
   at least one buffer memory; and
   at least one programmable current regulator, wherein the at least one buffer memory is coupled between the computing device and the at least one programmable current regulator, wherein the computing device is configured to load a string of output current values into the at least one buffer memory, wherein the at least one buffer memory is configured to sequentially feed each output current value to the at least one programmable current regulator, wherein the at least one programmable current regulator is configured to control current supplied to a plurality of electrodes based on the received output current values; and wherein the at least one programmable current regulator comprises:
   a digital to analog converter;
   a current regulator amplifier coupled to the digital to analog converter; and
   a field effect transistor coupled to the current regulator amplifier.

2. The waveform generation system of claim 1, wherein the at least one buffer memory comprises a first in first out buffer memory.

3. The waveform generation system of claim 1, wherein the at least one buffer memory comprises a plurality of buffer memories.

4. The waveform generation system of claim 1, wherein the at least one programmable current regulator comprises a plurality of programmable current regulators.

5. The waveform generation system of claim 1, wherein the waveform generation system is configured to generate a plurality of adjacent square wave pulses to form a continuous waveform.

6. A neurostimulation system comprising:
   a plurality of electrodes; and
   a waveform generation system coupled to the plurality of electrodes, the waveform generation system comprising:
   a computing device;
   at least one buffer memory; and
   at least one programmable current regulator, wherein the at least one buffer memory is coupled between the computing device and the at least one programmable current regulator, wherein the computing device is configured to load a string of output current values into the at least one buffer memory, wherein the at least one buffer memory is configured to sequentially feed each output current value to the at least one programmable current regulator, wherein the at least one programmable current regulator is configured to control current supplied to the plurality of electrodes based on the received output current values, and wherein the at least one programmable current regulator comprises:
   a digital to analog converter; and
   one of a programmable current source and a programmable current sink coupled to the digital to analog converter.

7. The neurostimulation system of claim 6, wherein the at least one buffer memory comprises a first in first out buffer memory.

8. The neurostimulation system of claim 6, wherein the at least one buffer memory comprises a plurality of buffer memories.

9. The neurostimulation system of claim 6, wherein the at least one programmable current regulator comprises a plurality of programmable current regulators.

10. The neurostimulation system of claim 6, wherein the waveform generation system is configured to generate a plurality of adjacent square wave pulses to form a continuous waveform.

11. A method of assembling a waveform generation system for use in an implantable pulse generator of a neurostimulation system, the method comprising:
   coupling at least one buffer memory to computing device; and
   coupling at least one programmable current regulator to the at least one buffer memory, wherein the computing device is configured to load a string of output current values into the at least one buffer memory, wherein the at least one buffer memory is configured to sequentially feed each output current value to the at least one programmable current regulator, wherein the at least one programmable current regulator is configured to control current supplied to a plurality of electrodes based on the received output current values, and wherein the at least one programmable current regulator includes a digital to analog converter, a current regulator amplifier coupled to the digital to analog converter, and a field effect transistor coupled to the current regulator amplifier.

12. The method of claim 11, wherein coupling at least one buffer memory comprises coupling a first in first out buffer memory.

13. The method of claim 11, wherein coupling at least one buffer memory comprises coupling a plurality of buffer memories.

14. The method of claim 11, wherein coupling at least one programmable current regulator comprises coupling a plurality of programmable current regulators.

* * * * *